(12) United States Patent
Matsumoto et al.

(10) Patent No.: US 7,727,320 B2
(45) Date of Patent: Jun. 1, 2010

(54) ANTHRAPYRIDONE COMPOUND, MAGENTA INK COMPOSITION AND COLORED MATTER

(75) Inventors: Hiroyuki Matsumoto, Kita-ku (JP); Noriko Kajiura, Kita-ku (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 383 days.

(21) Appl. No.: 11/794,638

(22) PCT Filed: Jan. 13, 2006

(86) PCT No.: PCT/JP2006/000378

§ 371 (c)(1),
(2), (4) Date: Jul. 2, 2007

(87) PCT Pub. No.: WO2006/075706

PCT Pub. Date: Jul. 20, 2006

(65) Prior Publication Data

US 2009/0285988 A1  Nov. 19, 2009

(30) Foreign Application Priority Data

Jan. 17, 2005  (JP) .............................. 2005-008918

(51) Int. Cl.
C09D 11/02 (2006.01)
B41J 2/01 (2006.01)
C07D 221/18 (2006.01)

(52) U.S. Cl. ........................ 106/31.47; 347/100; 546/76

(58) Field of Classification Search ............... 106/31.47, 106/31.77; 546/76; 347/100
See application file for complete search history.

(56) References Cited

U.S. PATENT DOCUMENTS

| | | | | |
|---|---|---|---|---|
| 6,471,760 B1 | 10/2002 | Matsumoto et al. | ...... | 106/31.47 |
| 6,530,985 B1 | 3/2003 | Matsumoto et al. | ...... | 106/31.47 |
| 6,645,283 B1 | 11/2003 | Matsumoto et al. | ...... | 106/31.47 |
| 6,648,952 B1 | 11/2003 | Matsumoto et al. | ...... | 106/31.47 |
| 6,852,154 B2 * | 2/2005 | Kitamura et al. | ......... | 106/31.47 |
| 6,929,361 B2 * | 8/2005 | Matsumoto et al. | ...... | 106/31.47 |
| 6,984,032 B2 * | 1/2006 | Kitamura et al. | ......... | 106/31.47 |
| 7,015,327 B2 | 3/2006 | Matsumoto et al. | ........... | 546/76 |
| 7,211,132 B2 * | 5/2007 | Oki et al. | ................. | 106/31.47 |
| 7,323,045 B2 * | 1/2008 | Hanmura et al. | ......... | 106/31.47 |
| 7,416,592 B2 * | 8/2008 | Kitamura et al. | ......... | 106/31.47 |
| 2004/0239739 A1 | 12/2004 | Matsumoto et al. | ......... | 347/100 |
| 2007/0266890 A1* | 11/2007 | Taguchi et al. | ............ | 106/31.47 |
| 2008/0257209 A1* | 10/2008 | Kitamura et al. | ......... | 106/31.48 |
| 2008/0274284 A1* | 11/2008 | Fujimoto et al. | ......... | 106/31.47 |
| 2009/0000511 A1* | 1/2009 | Kitamura et al. | ......... | 106/31.47 |

FOREIGN PATENT DOCUMENTS

| | | |
|---|---|---|
| JP | 59-74173 | 4/1984 |
| JP | 2-16171 | 1/1990 |
| JP | 2000-109464 | 4/2000 |
| JP | 2000-169776 | 6/2000 |
| JP | 2000-191660 | 7/2000 |
| JP | 2001-72884 | 3/2001 |
| JP | 2001-139836 | 5/2001 |
| JP | 2003-192930 | 7/2003 |
| JP | 2005/307068 | * 11/2005 |
| WO | WO 03/027185 | * 4/2003 |

OTHER PUBLICATIONS

Machine translation of JP 2005/307068, Nov. 2005.*
International Search Report dated Apr. 11, 2007.

* cited by examiner

*Primary Examiner*—Helene Klemanski
(74) *Attorney, Agent, or Firm*—Nields, Lemack & Frame, LLC

(57) ABSTRACT

The present invention relates to an anthrapyridone compound represented by the following Formula (1)

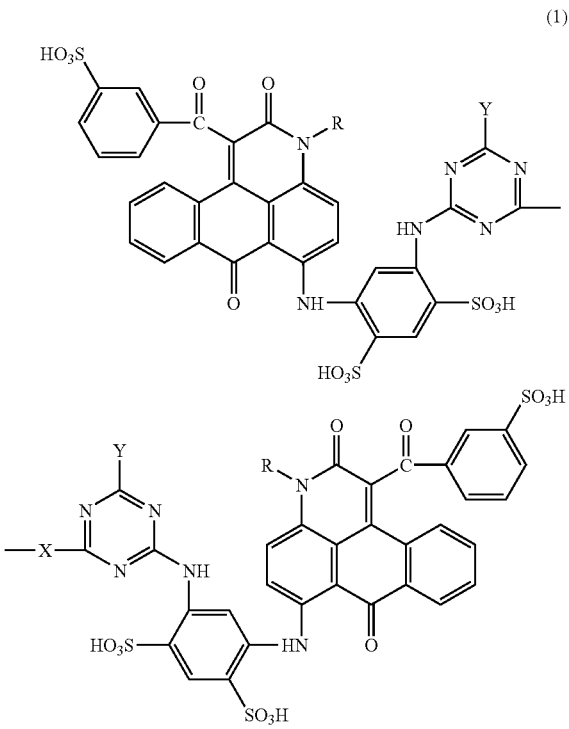

wherein, R represents a hydrogen atom, an alkyl group, a hydroxy lower alkyl group, a cyclohexyl group, a mono- or dialkylaminoalkyl group or a cyano lower alkyl group, X represents a cross linking group, Y represents a phenoxy group having 1 or 2 carboxyl groups in free acid form and a magenta ink composition comprising the same, and provides magenta coloring matter and a magenta ink composition which have hue with high vividness suitable for inkjet recording, gives good fastness to a recorded article and are excellent in storage stability.

17 Claims, No Drawings

ANTHRAPYRIDONE COMPOUND, MAGENTA INK COMPOSITION AND COLORED MATTER

TECHNICAL FIELD

The present invention relates to a novel anthrapyridone compound, a magenta ink composition comprising the anthrapyridone compound and a colored matter obtained by using the same.

BACKGROUND OF THE INVENTION

For a recording method by means of an inkjet printer which is a typical method among various color recording methods, various methods of discharging ink have been developed, and any of them performs recording by generating ink droplets and depositing them onto various record-receiving materials (such as paper, film and cloth). This method has been rapidly prevailing lately and is expected to grow remarkably in the future because of such features as little noise generation due to no contact of a recording head with a record-receiving material and easiness in downsizing, speedup and colorization.

Conventionally, as an ink for a fountain pen or a felt pen and an ink for inkjet recording, a water-based ink dissolving a water-soluble dye in an aqueous medium has been used, and in these water-soluble inks, a water-soluble organic solvent is generally added to prevent ink from clogging at a pen tip or an inkjet nozzle. These conventional inks are required to provide a recorded image with sufficient density, not to clog at a pen tip or an inkjet nozzle, to dry quickly on a record-receiving material, to bleed less, to have good storage stability, and the like, and a formed image is required to have fastnesses such as water fastness, light fastness, and moisture fastness.

Meanwhile, when an image or character information on a color display of a computer is recorded in color by an inkjet printer, they are generally rendered using subtractive color mixing of four color inks, yellow (Y), magenta (M), cyan (C), and black (K). In order to reproduce, as faithfully as possible, their hues of an image by additive color mixing of red (R), green (G) and blue (B) on a CRT display and the like, with an image by subtractive color mixing, each of Y, M and C is desired to have such hue as close to each standard as possible and vividness. In addition, it is required that an ink composition to be used for it is stable in storage for a long period of time, and that an printed image has a high concentration and excellent fastnesses such as water fastness, light fastness and gas fastness.

Application of an inkjet printer is expanding in range from a compact printer for office to a large printer for industry, and fastnesses such as water fastness, moisture fastness, light fastness and gas fastness are required more than ever. Water fastness has been improved substantially by coating organic or inorganic fine particles which can adsorb coloring matter in ink, such as porous silica, cation-based polymer, aluminasol or special ceramics on the surface of paper, together with PVA resin and the like. Moisture fastness means durability against the phenomenon that coloring matter of dye in record-receiving material bleeds when colored record-receiving material is stored under a high humid atmosphere. Bleeding of coloring matter of dye leads to extremely deteriorating an image quality level especially in an image requiring high-definition image quality like photo tone, so it is important to cause as little bleeding as possible. Because any technique to improve light fastness greatly has not established yet and especially many types of coloring matter of magenta among 4 primary colors of Y, M, C and K are originally weak in light fastness, its improvement is an important problem. In addition, along with the recent penetration of digital cameras, the chance to print a photo at home is also increased, and discoloration of a printed image caused by oxidizing gas in the air when the obtained printed article is stored is acknowledged as a problem. Oxidizing gas has a property to react with dye on or in recording paper to discolor or fade a printed image. Among oxidizing gases, ozone gas is considered as the main causative substance to promote the phenomenon of fading an inkjet recorded image. Because the phenomenon of discoloration or fading is characteristics of inkjet image, improvement of ozone gas fastness is also an important problem, as well as improvement of light fastness.

As a coloring matter structure of coloring matter for magenta to be used water-soluble ink for inkjet recording, xanthene-based coloring matter and azo-based coloring matter using H acid is typical. Xanthene-based one is, however, very excellent in hue and vividness but very inferior in light fastness. Some types of azo-based coloring matter using H acid are good in terms of hue and water fastness but inferior in light fastness, gas fastness and vividness. Some magenta dyes of this type has been developed to have excellent vividness and light fastness, but their level of light fastness is still inferior to that of dye of such other hues as cyan dye, yellow dye and the like which are typified by copper phthalocyanine-based coloring matter.

Anthrapyridone-based coloring matter is exemplified as a coloring matter structure of coloring matter for magenta which is excellent in vividness and light fastness (for example, Patent Literatures 1 to 8), however, any type of anthrapyridone-based coloring matter that satisfies all of hue, vividness, light fastness, water fastness, gas fastness and solution stability has not been provided yet.

Patent Literature 1: JP 59-74173 A (Page 1 to 3)

Patent Literature 2: JP 2-16171 A (Page 1 and 5 to 7)

Patent Literature 3: JP 2000-109464 A (Page 1 to 2 and 8 to 12)

Patent Literature 4: JP 2000-169776 A (Page 1 to 2 and 6 to 9)

Patent Literature 5: JP 2000-191660 A (Page 1 to 3 and 11 to 14)

Patent Literature 6: JP 2001-72884 A (Page 1 to 2 and 8 to 11)

Patent Literature 7: JP 2001-139836 A (Page 1 to 2 and 7 to 12)

Patent Literature 8: JP 2003-192930 A (Page 22 and 36 to 37)

DISCLOSURE OF THE INVENTION

Problems to be Solved by the Invention

An object of the present invention is to provide coloring matter (compound) for magenta which has high solubility in water and suitable hue and vividness for inkjet recording and also is excellent in light fastness, moisture fastness and gas fastness in a recorded article, and an ink composition comprising the same.

Means of Solving the Problems

The inventors of the present invention intensively studied a way to solve the above problems and have found that an anthrapyridone compound represented by a specified formula can solve the above problems to complete the present invention.

That is, the present invention relates to:

(1) An anthrapyridone compound represented by the following Formula (1)

[KA 1]

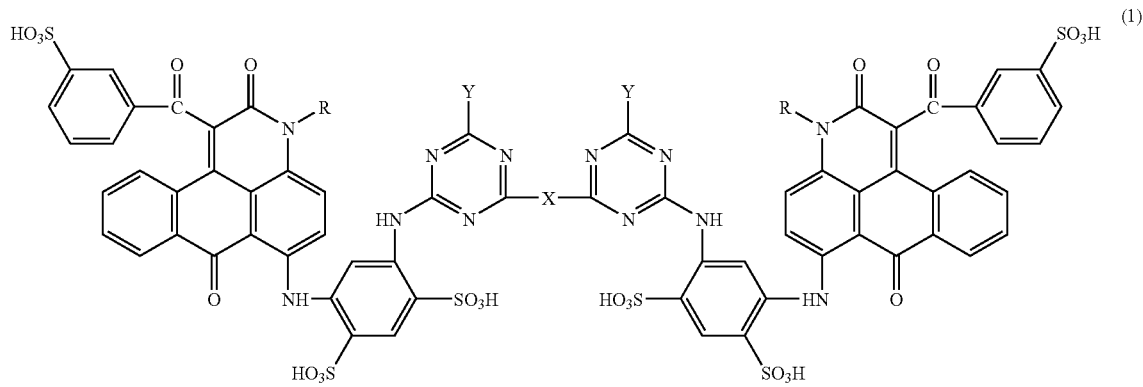

(wherein, R represents a hydrogen atom, an alkyl group, a hydroxy lower alkyl group, a cyclohexyl group, a mono- or dialkylaminoalkyl group or a cyano lower alkyl group, X represents a cross linking group, Y represents a group represented by the following Formula (2),

[KA 2]

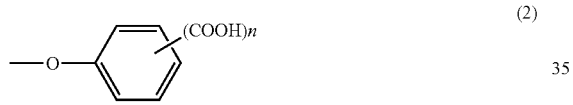

(wherein, n represents an integer of 1 or 2) respectively)

in free acid form, (2) The anthrapyridone compound according to the above (1), which is represented by the following Formula (3)

[KA 3]

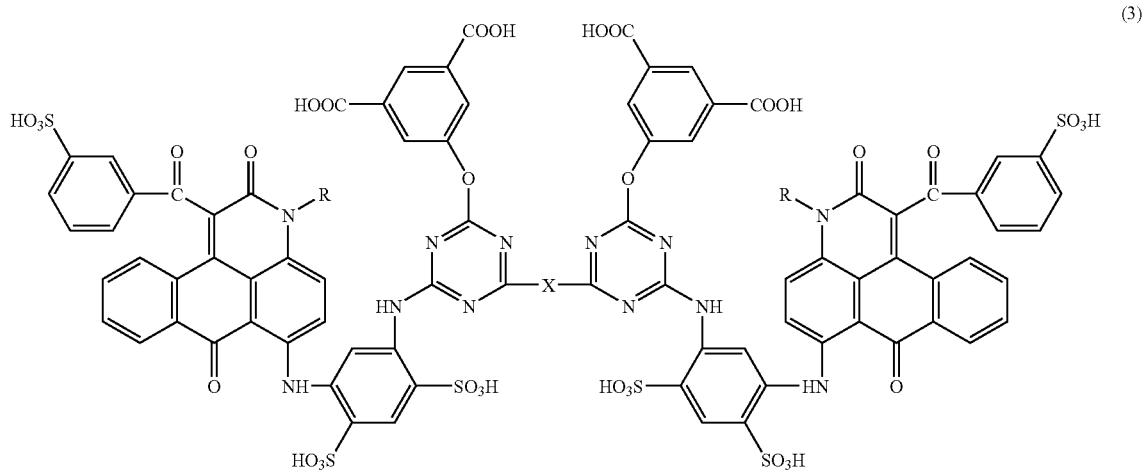

(wherein, R and X have the same meanings as in Formula (1))

in free acid form, (3) The anthrapyridone compound according to the above (1), which is represented by Formula (4)

[KA 4]

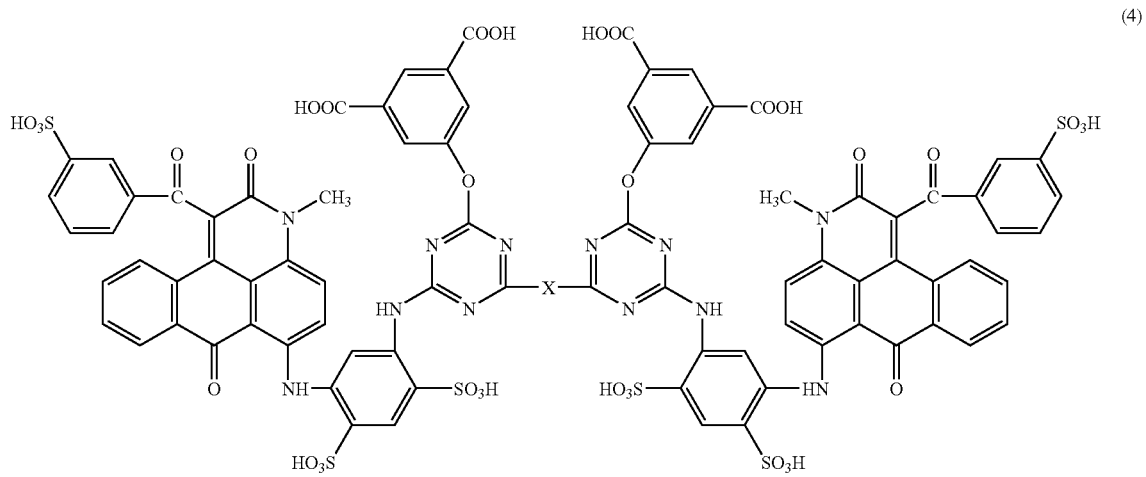

(4)

(wherein, X has the same meaning as in Formula (1)) in free acid form, (4) The anthrapyridone compound according to any one of the above (1) to (3), wherein the cross linking group X is a group represented by the following formula, —N(H)$m$(-A-)$n_1$N(H)$m$-, —S-A-S—, —NH-A-S— or —O-A-O—

(wherein, A is a residual group of divalent hydrocarbon with a carbon number of 1 to 20 and can comprise a nitrogen atom, an oxygen atom or a sulfur atom, $n_1$ represents 0 to 2, m represents 1 or 0, m represents 1 when $n_1$ is 0 or 1, and m represents 0 when $n_1$ is 2), (5) The anthrapyridone compound according to any one of the above (1) to (3), wherein the cross linking group X is a diaminoalkylene group, (6) An anthrapyridone compound represented by the following Formula (5)

[KA 5]

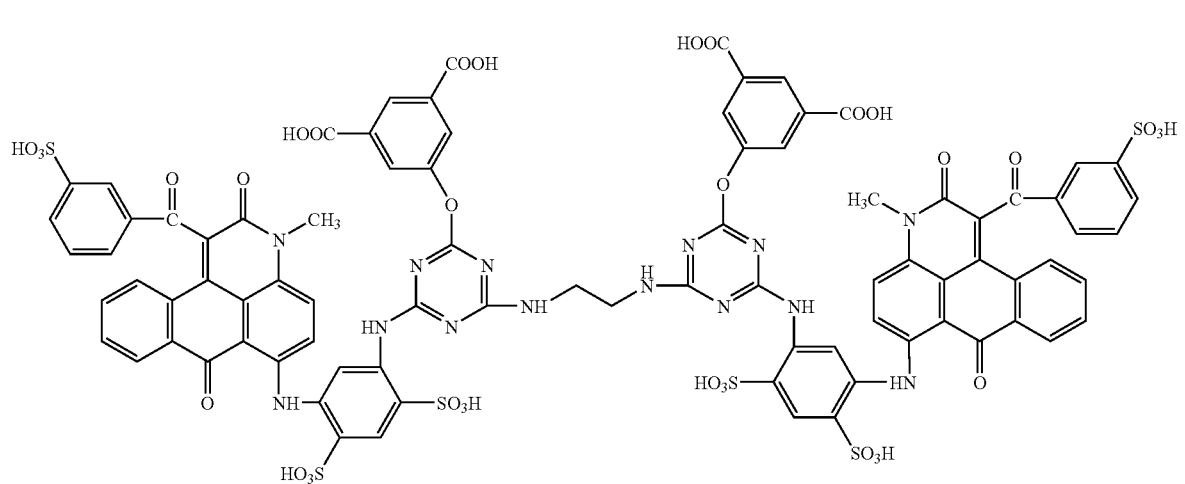

(5)

in free acid form, (7) An anthrapyridone compound represented by the following Formula (6)

[KA 6]

(6)

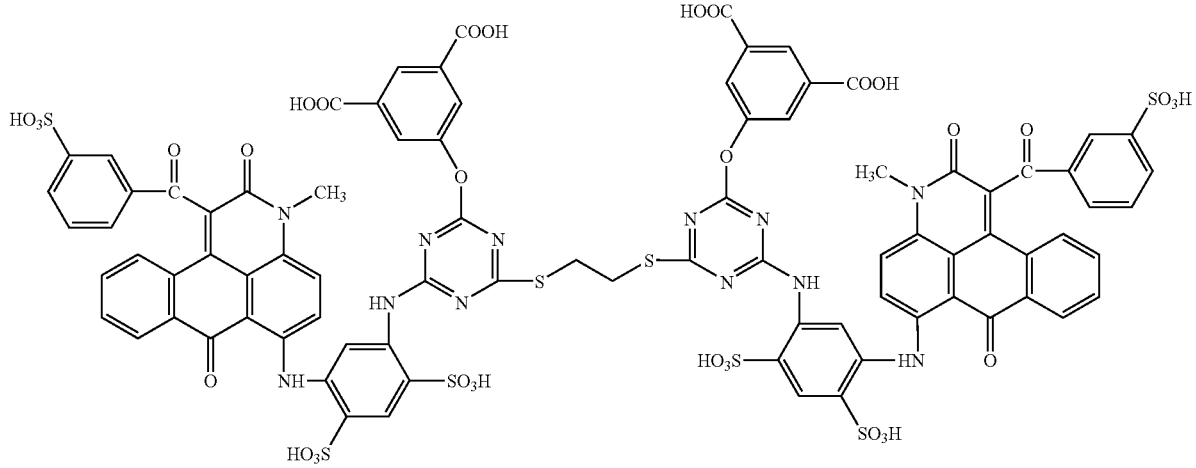

in free acid form, (8) A magenta ink composition characterized by comprising the anthrapyridone compound according to any one of the above (1) to (7), (9) The magenta ink composition according to the above (8), which comprises water and a water-soluble organic solvent,

(10) The magenta ink composition according to the above (9), which is for inkjet,

(11) The magenta ink composition according to any one of the above (8) to (10), wherein the content of inorganic substance in an anthrapyridone compound according to any one of the above (1) to (7) is not more than 1 weight %,

(12) The magenta ink composition according to any one of the above (8) to (11), wherein the content of the anthrapyridone compound according to any one of the above (1) to (7) is 0.1 to 20 weight %,

(13) An inkjet recording method characterized by using the magenta ink composition according to any one of the above (8) to (12) as an ink in an inkjet recording method where recording is performed on a record-receiving material by discharging an ink droplet in response to a recording signal,

(14) The inkjet recording method according to the above (13), wherein the record-receiving material is a sheet for information transmission,

(15) The inkjet recording method according to the above (14), wherein the sheet for information transmission has an ink-receiving layer comprising a porous white inorganic substance,

(16) A colored article which is colored with the magenta ink composition for inkjet recording according to any one of the above (8) to (12),

(17) The colored article according to the above (16), wherein coloring is performed by an inkjet printer,

(18) An inkjet printer wherein a container comprising the magenta ink composition according to any one of the above (8) to (12) is loaded,

(19) The anthrapyridone compound according to the above (1), wherein in Formula (1) R represents a hydrogen atom or a C1 to C4 alkyl which may be substituted by a hydroxyl group or a di(C1 to C4) alkylamino group, X is a group represented by -M1-A1-M2-(each of M1 and M2 independently represents, NH, an oxygen atom or a sulfur atom, and A1 represents a single bond; a C1 to C6 alkylene; phenylene which may be substituted by a C1 to C4 alkyl group; methylenedicyclohexane-diyldiimino group which may be substituted by a C1 to C4 alkyl group on a cyclohexyl group; a diphenylether-diyl group or a diphenylmethanediyl group) or a 1,4-piperazinediyl group,

(20) The compound according to the above (1), wherein in Formula (1) R is a methyl group, X is NH—NH, S—$CH_2CH_2$—S, NH—$CH_2CH_2$—NH or NH-cyclohexyl-$CH_2$-cyclohexyl-NH,

(21) The anthrapyridone compound according to the above (1), wherein in Formula (2) n is 2,

(22) The anthrapyridone compound according to any one of the above (19) to (20), wherein in Formula (1) Y is a 3,5-dicarboxyl-phenoxy group.

EFFECT OF THE INVENTION

An anthrapyridone compound represented by Formula (1) of the present invention has characteristics to express a highly vivid and brilliant hue on inkjet recording paper and be excellent in water-solubility and good in filtration property on a membrane filter in the process of producing an ink composition. In an ink composition of the present invention using this compound, crystal precipitation, change in physical property, color change after storage for a long period of time and the like doesn't occur, and storage stability is good. A printed article using a magenta ink for inkjet recording comprising an anthrapyridone compound of the present invention exhibits an ideal magenta hue without selecting a record-receiving material (paper, film and the like). A magenta ink composition of the present invention can also faithfully reproduce the hue of a photo tone color image on paper. In addition, when recording is performed on a record-receiving material surface of which is coated with inorganic fine particles like photo quality inkjet paper (film), it provides good fastnesses such as light fastness, ozone fastness and moisture fastness and excellent storage stability for a long period of time of a photo tone recorded image. Thus, an anthrapyridone compound represented by Formula (1) is extremely useful as coloring matter to be used for an ink for inkjet recording.

BEST MODE FOR CARRYING OUT THE INVENTION

The present invention will be described in detail hereinafter. In the present invention, unless otherwise specified, a sulfonic acid group and a carboxy group are shown in free acid form.

An anthrapyridone compound of the present invention is represented by the following Formula (1)

hydroxyl group or a di lower alkylamino group as a substituent, more preferably an alkyl group with a carbon number of 1 to 4 which may has a hydroxyl group or a di lower alkylamino group as a substituent, most preferably a methyl group.

In Formula (1), Y represents a carboxy-substituted phenoxy group represented by the above Formula (2). n in Formula (2) can be any one of 1 or 2, preferably 2. Specific examples of the carboxy-substituted phenoxy group in Formula (2) include a 4-carboxyphenoxy group and a 3,5-dicarboxyphenoxy group, preferably a 3,5-dicarboxyphenoxy group.

In Formula (1), X is a cross linking group, and its specific examples include —N(H)m(-A-)n$_1$N(H)m-, —S-A-S—,

[KA 7]

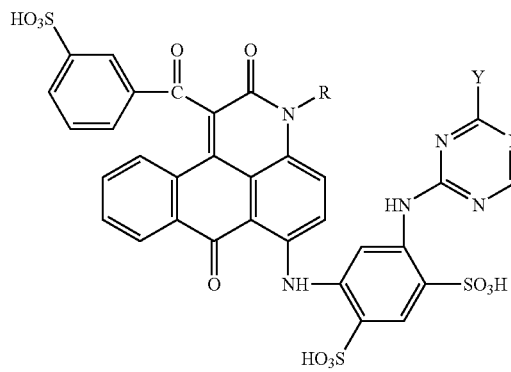
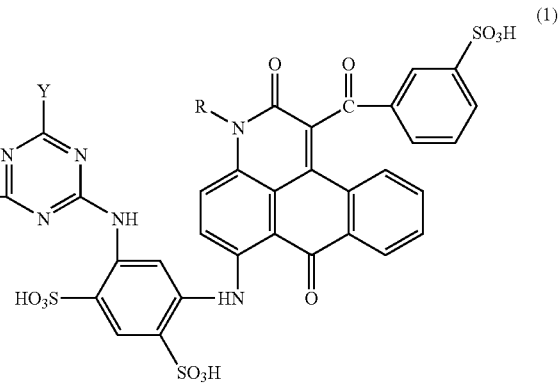
(1)

(wherein, R represents a hydrogen atom, an alkyl group, a hydroxy lower alkyl group, a cyclohexyl group, a mono- or dialkylaminoalkyl group or a cyano lower alkyl group, X represents a cross linking group, and Y represents a group represented by the following Formula (2))

[KA 8]

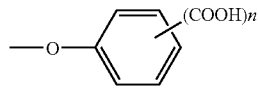
(2)

(wherein, n represents an integer of 1 or 2).

In Formula (1), R represents a hydrogen atom, an alkyl group, a hydroxy lower alkyl group, a cyclohexyl group, a mono- or dialkylaminoalkyl group or a cyano lower alkyl group. The alkyl group includes, for example, an alkyl group with a carbon number of 1 to 8 such as a methyl group, an ethyl group, a n-propyl group, an iso-propyl group, a n-butyl group, a tert-butyl group, a n-hexyl group, a cyclohexyl group, a n-octyl group. The alkyl for a hydroxy lower alkyl group and a cyano lower alkyl group includes, for example, ethyl, propyl and the like, preferably ethyl. In this connection, a lower alkyl referred herein represents a C1 to C4 alkyl group unless otherwise specified. Preferable R includes an alkyl group with a carbon number of 1 to 8 which may has a —NH-A-S— or —O-A-O— (in these formulas, A is a residual group of divalent hydrocarbon with a carbon number of 1 to 20 and may comprise a nitrogen atom, an oxygen atom or a sulfur atom, n$_1$ represents 0 to 2, m is 1 or 0, m represents 1 when n$_1$ is 0 or 1, and m represents 0 when n$_1$ is 2). In —N(H)m(-A-)n$_1$ N(H)m-, in the case of n$_1$=2 and m=0, said formula represents a piperazinediyl group. Preferable X includes —N(H)m(-A-)n$_1$N(H)m- and —S-A-S—. Specific examples of A here include C1 to C6 (poly) methylene, phenylene which may have a substituent, xylylene, methylenedicyclohexane-diyl, methylene bis(methylcyclohexane-diyl), and cyclohexane-diyl-dimethylene, more preferably dimethylene, hexamethylene, 1,3-xylylene, methylenedicyclohexane-4,1-diyl, methylene bis(2-methylcyclohexane)-4,1-diyl and cyclohexane-1,3-diyl-dimethylene. Especially preferable A includes a C1 to C4 alkylene group, above all preferably an ethylene group.

Otherwise, optionally preferable X includes a group represented by a formula -M1-A1-M2-, or a 1,4-piperazinediyl group. In the formula -M1-A1-M2-, each of M1 and M2 independently represents NH, an oxygen atom or a sulfur atom, A1 is a single bond; C1 to C6 alkylene; phenylene which may be substituted by a C1 to C4 alkyl group; a methylenedicyclohexane-diyldiimino group which may be substituted by a C1 to C4 alkyl group on a cyclohexyl group; a diphenylether-diyl group or a diphenylmethanediyl group.

Preferable X in this case includes NH—NH, S—CH$_2$CH$_2$—S, NH—CH$_2$CH$_2$—NH or NH-cyclohexyl-CH$_2$-cyclohexyl-NH, and the like.

Preferable combinations of R, Y, and X in the above Formula (1) include combinations of the above preferable ones, more preferably, for example, R is a hydrogen atom or a methyl group, more preferably a methyl group, Y is a 4-carboxyphenoxy group or a 3,5-dicarboxyphenoxy group, more preferably a 3,5-dicarboxyphenoxy group, and X is a 1,2-ethanediimino group, a methylenedicyclohexane-4,1-diyldiimino group or a hydrazo group, more preferably a 1,2-ethanediimino group.

A compound represented by Formula (1) is shown in free acid form, so the present invention includes all compounds showing the structure of Formula (1) in free acid form, and for example, a salt of a compound represented by Formula (1) is included in the present application.

A salt of a compound represented by Formula (1) is an inorganic or organic cationic salt. Specific examples of the salt include a lithium salt, a sodium salt, a potassium salt or an ammonium salt represented by the following Formula (A)

[KA 9]

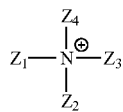

(A)

(wherein, each of $Z_1$ to $Z_4$ independently represents a hydrogen atom, an alkyl group, a hydroxyalkyl group or a hydroxyalkoxyalkyl group).

Examples of the alkyl group in $Z_1$ to $Z_4$ in Formula (A) include a methyl group, an ethyl group and the like, examples of the hydroxyalkyl group include a hydroxymethyl group, a 2-hydroxyethyl group, a 3-hydroxypropyl group, a 2-hydroxypropyl group, a 4-hydroxybutyl group, a 3-hydroxybutyl group, a 2-hydroxybutyl group and the like, and furthermore, examples of the hydroxyalkoxyalkyl group include a hydroxyethoxymethyl group, a 2-hydroxyethoxyethyl group, a 3-hydroxyethoxypropyl group, a 3-hydroxyethoxybutyl group, a 2-hydroxyethoxybutyl group and the like.

Preferable ones among them include a sodium salt, a potassium salt, a lithium salt, a monoethanolamine salt, a diethanolamine salt, a triethanolamine salt, a monoisopropanolamine salt, a diisopropanolamine salt, a triisopropanolamine salt, an ammonium salt and the like. Among them, especially preferable ones are salts of lithium, ammonium and sodium.

The above salts can be obtained as below.

For example, a sodium chloride is added to a reaction solution containing a compound of Formula (1) obtained by the reaction as described below or a solution dissolving a cake containing an objective compound (a compound of Formula (1)) or a dried one thereof in water for salting out and then filtration to obtain a sodium salt as a wet cake. Further, after the wet cake is dissolved in water again and then hydrochloric acid is added thereto to adjust the pH at 1 to 2 to obtain a crystal, the crystal can be filtered to obtain a compound of Formula (1) in free acid form (or partially as sodium salt itself. Furthermore, while the free acid wet cake being stirred together with water, for example, potassium hydroxide, lithium hydroxide, ammonia water or a compound represented by Formula (A) are added thereto to turn it to alkaline, and to obtain each corresponding potassium salt, lithium salt, ammonium salt and organic salt. Among the salts, especially preferable ones are salts of lithium, ammonium and sodium as described above.

Next, specific examples of an anthrapyridone compound represented by Formula (1) of the present invention are shown in Table 1. In Table 1, (K) means a monocarboxy group and 2(K) means a dicarboxy group, respectively.

TABLE 1

| No. | R | X | Y |
|---|---|---|---|
| 1 | CH$_3$ | 1,2-ethanediimino | 3,5-2(K)-phenoxy |
| 2 | CH$_3$ | methylene dicyclohexane-4,1-diyldiimino | 3,5-2(K)-phenoxy |
| 3 | CH$_3$ | hydrazo | 3,5-2(K)-phenoxy |
| 4 | CH$_3$ | 1,2-ethanediimino | 4-(K)-phenoxy |
| 5 | CH$_3$ | 1,4-butanediimino | 3,5-2(K)-phenoxy |
| 6 | CH$_3$ | 1,6-hexanediimino | 3,5-2(K)-phenoxy |
| 7 | CH$_3$ | m-xylylene diimino | 3,5-2(K)-phenoxy |
| 8 | CH$_3$ | 1,4-piperazinediyl | 3,5-2(K)-phenoxy |
| 9 | CH$_3$ | —S—CH$_2$CH$_2$—NH— | 3,5-2(K)-phenoxy |
| 10 | CH$_3$ | —S—CH$_2$CH$_2$—S— | 3,5-2(K)-phenoxy |
| 11 | H | 1,2-ethanediimino | 3,5-2(K)-phenoxy |
| 12 | C$_2$H$_5$ | 1,2-ethanediimino | 3,5-2(K)-phenoxy |
| 13 | C$_2$H$_4$OH | 1,2-ethanediimino | 3,5-2(K)-phenoxy |
| 14 | C$_4$H$_9$ | 1,2-ethanediimino | 3,5-2(K)-phenoxy |
| 15 | cyclohexyl | 1,2-ethanediimino | 3,5-2(K)-phenoxy |
| 16 | C$_3$H$_6$N(C$_2$H$_5$)$_2$ | 1,2-ethanediimino | 3,5-2(K)-phenoxy |
| 17 | CH$_3$ | methylenebis(2-methylcyclohexane-4,1-diyldiimino) | 3,5-2(K)-phenoxy |
| 18 | H | 1,2-ethanediimino | 3,5-2(K)-phenoxy |
| 19 | H | 1,2-ethanediimino | 4-(K)-phenoxy |

TABLE 1-continued

| No. | R | X | Y |
| --- | --- | --- | --- |
| 20 | $CH_3$ | 1,4-dioxyphenylene | 3,5-2(K)-phenoxy |
| 21 | $CH_3$ | 4,4'-dioxydiphenylether | 3,5-2(K)-phenoxy |
| 22 | $CH_3$ | 4,4'-dioxydiphenylmethane | 3,5-2(K)-phenoxy |

An anthrapyridone compound represented by Formula (1) of the present invention can be produced by, for example, the following method.

That is, 2 mols of a compound represented by the following Formula (7)

[KA 10]

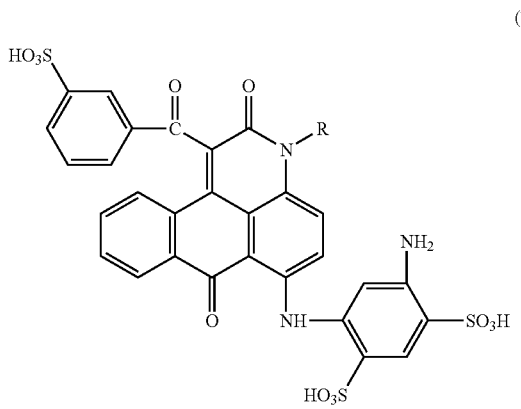

(7)

(wherein, R has the same meaning as in the above Formula (1))

and 2 to 2.4 mols of 2,4,6-trichloro-S-triazine (cyanuric chloride) are reacted in water at pH 2 to 7 at a reaction temperature of 5 to 35° C. for 2 to 8 hours to obtain a compound represented by the following Formula (8),

[KA 11]

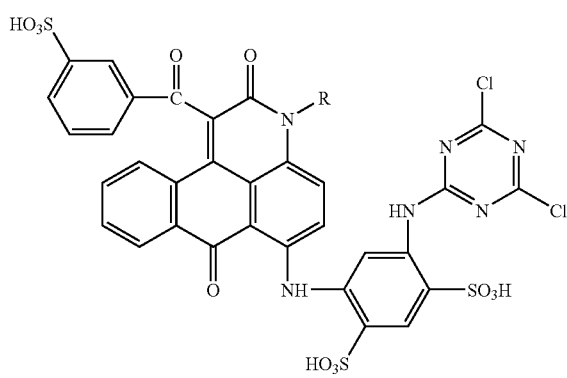

(8)

(wherein, R has the same meaning as in Formula (1))

as a first condensation product. Said resulting compound is reacted with 2 mols of carboxy-substituted phenols corresponding to a group represented by Formula (2) at pH 7 to 9 at a reaction temperature of 5 to 90° C. for 10 minutes to 5 hours to obtain a compound represented by the following Formula (9)

[KA 12]

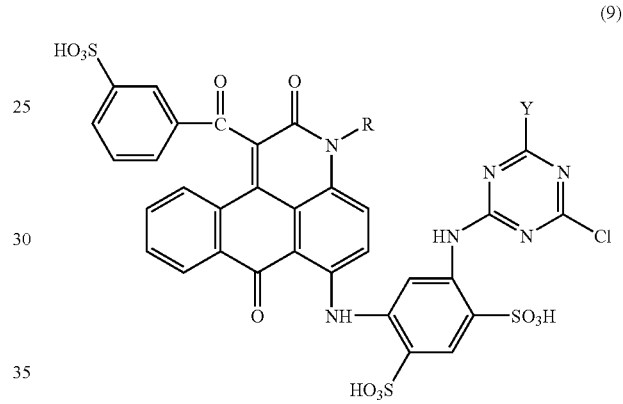

(9)

(wherein R and Y have the same meanings as in Formula (1))

as a second condensation product.

The above carboxy-substituted phenols include hydroxybenzoic acid, hydroxyisophthalic acid and the like.

Subsequently, the compound represented by Formula (9) obtained above is reacted with a compound corresponding to a cross linking group X, to obtain an objective compound of Formula (1) (represented newly by Formula (10) as shown below).

For example, in order to obtain a compound where a cross linking group X is a group having amino groups at the both ends, the compound represented by the above Formula (9) is reacted with 1 mol of a diamino compound of the following Formula (14)

$$HN(H)m(-A-)n_1N(H)mH \qquad (14)$$

(wherein, A has the same meaning as in Formula (1), m and $n_1$ have the same meanings described in the above section of a cross linking group)

for 10 minutes to 8 hours under conditions that the pH is 8 to 10 and the temperature is approximately 50 to 100° C., to obtain a compound where X is the above —N(H)m(-A-)$n_1$N (H)m- in the following Formula (10) (same as Formula (1))

[KA 13]

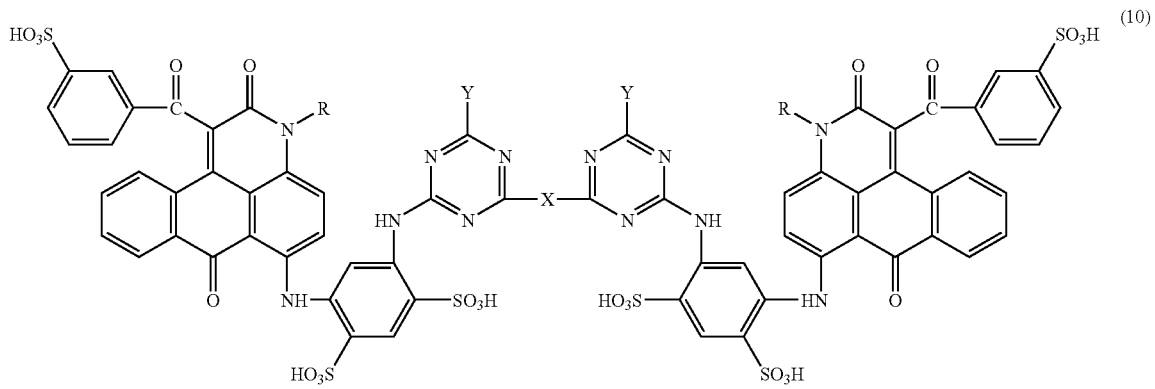
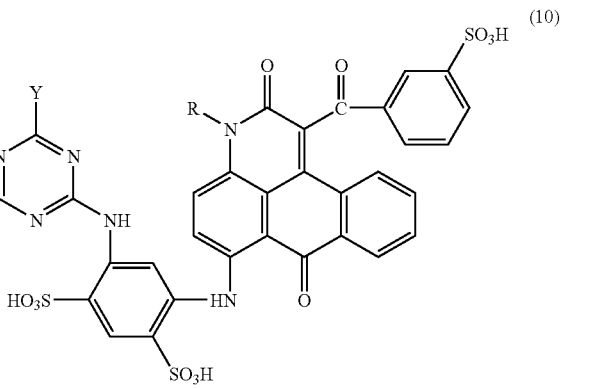

(wherein, R, X and Y have the same meanings as in Formula (1))

as a third condensation product.

A compound represented by Formula (14) includes, for example, C1 to C20 hydrocarbon diamine such as hydrazine, ethylenediamine, butylenediamine, hexylenediamine, xylylenediamine or piperazine or methylene dicyclohexanediamine which may have lower alkyl substitution on a cyclohexane ring A compound represented by the following Formula

HS-A-SH, HS-A-$NH_2$, HO-A-OH (wherein, A has the same meaning as above)

is used instead of a compound represented by the above Formula (14) for condensation reaction by a conventional method to obtain a compound where the cross linking group X in the above Formula (10) is —S-A-S—, —S-A-NH— and —O-A-O—, respectively.

The above thioglycol includes alkylene thioglycol such as ethylene thioglycol. Glycol includes C1 to C20 hydrocarbon glycol which may contain a hetero atom such as an oxygen atom, such as ethyleneglycol, dihydroxybenzene, and di(hydroxyphenyl)ether and di(hydroxyphenyl)methane which have hydroxy substitution on each benzene ring. Mercapto-substituted alkylamine includes mercapto-substituted ethylamine and the like.

The sequence of condensation can be decided arbitrarily according to reactivity of each compound and not limited to the above.

In the meanwhile, an anthrapyridone compound represented by Formula (7) can be obtained as described below for example. That is, 1 mol of an anthraquinon compound represented by the following Formula (11)

[KA 14]

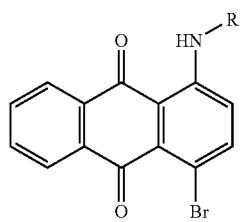

(11)

(wherein, R has the same meaning as in Formula (1))

is reacted with 1.1 to 3 mols of ethyl benzoylacetate in a polar solvent such as xylene at 130 to 180° C. for 5 to 15 hours in the presence of a basic compound such as sodium carbonate to obtain a compound represented by the following Formula (12)

[KA 15]

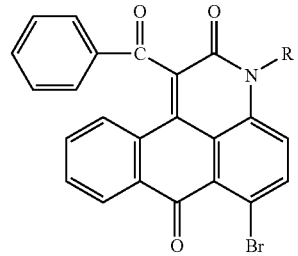

(12)

(wherein, R has the same meaning as in Formula (1)).

Subsequently, 1 mol of a compound represented by Formula (12) is condensed with 1 to 5 mols of meta-amino acetanilide by Ullmann reaction in an aprotic polar organic solvent such as N,N-dimethylformamide at 110 to 150° C. for 2 to 6 hours in the presence of a base such as sodium carbonate and a copper catalyst such as copper acetate to obtain a compound represented by the following Formula (13)

[KA 16]

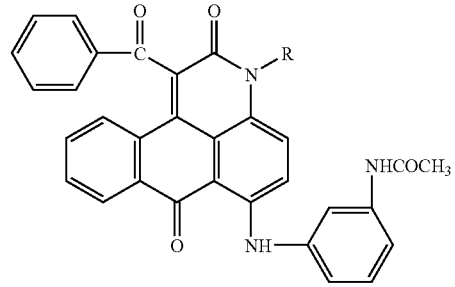

(13)

(wherein, R has the same meaning as in Formula (1)).

Subsequently, a compound represented by Formula (13) is subjected to sulfonation and hydrolysis of an acetylamino group in 8 to 15 weight % of fuming sulfuric acid at 50 to 120° C. to obtain an anthrapyridone compound represented by the following Formula (7)

[KA 17]

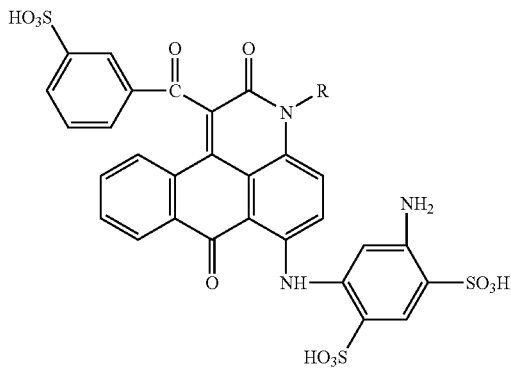

(7)

(wherein, R has the same meaning in Formula (1)).

An anthrapyridone compound of the present invention is suitable for dyeing natural and synthetic fiber materials or mixed fabrics as magenta coloring matter for ink, and further these compounds are suitable for producing an ink for writing tools and an ink composition for inkjet recording.

As a compound represented by the above Formula (1), coloring matter material with less content of inorganic substance such as a chloride of metal cation and a sulfate salt is preferably used, and the content is, for example, not more than approximately 1 weight % only as guide. To produce coloring matter material with less inorganic substance, for example, desalting treatment may be conducted by a usual method such as a method by reverse osmosis membrane.

An ink composition of the present invention is produced by dissolving a compound represented by Formula (1) in water or an aqueous solvent (water containing a water-soluble organic solvent as described below), otherwise a reaction solution containing a compound represented by Formula (1) of the present invention can be used directly to produce an ink composition. In addition, an objective substance is isolated from the reaction solution and dried, for example, by spray drying, and then also processed into an ink composition. An ink composition for recording of the present invention contains typically 0.1 to 20 weight % of a compound of the present invention, preferably 1 to 15 weight %, more preferably 2 to 10 weight %. An ink composition of the present invention may contain 0 to 30 weight % of a water-soluble organic solvent and 0 to 5 weight % of an ink preparation agent, respectively. The rest is water.

Specific examples of a water-soluble organic solvent to be used in the present invention include, for example, C1 to C4 alkanol such as methanol, ethanol, n-propanol, isopropanol, n-butanol, isobutanol, sec-butanol, tert-butanol; carboxylic acid amide such as N,N-dimethylformamide or N,N-dimethylacetamide; lactam such as 2-pyrrolidone or N-methyl-2-pyrrolidone; cyclic urea such as 1,3-dimethylimidazolidine-2-one or 1,3-dimethylhexahydropyrimid-2-one; ketone or keto alcohol such as acetone, methylethylketone, or 2-methyl-2-hydroxypentan-4-one; cyclic ether such as tetrahydrofuran or dioxane; monomer, oligomer or polyalkylene glycol or thioglycol having a (C2 to C6) alkylene unit such as ethylene glycol, 1,2- or 1,3-propylene glycol, 1,2- or 1,4-butylene glycol, 1,6-hexylene glycol, diethylene glycol, triethylene glycol, tetraethylene glycol, dipropylene glycol, thiodiglycol, polyethylene glycol or polypropylene glycol; polyol (triol) such as glycerin or hexane-1.2.6-triol; (C1 to C4) alkylether of polyhydric alcohol such as ethylene glycol monomethyl ether or ethylene glycol monoethyl ether, diethylene glycol monomethyl ether, diethylene glycol monobutyl ether (butyl carbitol) or diethylene glycol monoethyl ether or triethylene glycol monomethyl ether or triethylene glycol monoethyl ether; γ-butyrolactone; dimethylsulfoxide or the like. These water-soluble organic solvents are used alone or in mixture thereof.

Preferable ones among them are 2-pyrrolidone, N-methyl-2-pyrrolidone, mono-, di- or triethylene glycol and dipropylene glycol, more preferably 2-pyrrolidone, N-methyl-2-pyrrolidone and diethylene glycol.

Hereinafter, ink preparation agents to be used in preparing an ink composition of the present invention will be explained. Specific examples of the ink preparation agents include, for example, an antiseptic and fungicide, a pH modifier, a chelating agent, an antirust agent, a water-soluble ultraviolet absorbent, a water-soluble polymer compound, a dye-dissolving agent, a surfactant, and the like.

The antiseptic and fungicide includes compounds of, for example, an organic sulfur type, an organic nitrogen sulfur type, an organic halogen type, a haloallylsulfone type, an iodopropargyl type, an N-haloalkylthio type, a nitrile type, a pyridine type, an 8-oxyquinoline type, a benzothiazole type, an isothiazoline type, a dithiol type, a pyridine oxide type, a nitropropane type, an organic tin type, a phenol type, a quaternary ammonium salt type, a triazine type, a thiadiazine type, an anilide type, an adamantane type, a dithiocarbamate type, a brominated indanone type, a benzyl bromoacetate type, an inorganic salt type and the like. The organic halogen type compound includes, for example, sodium pentachlorophenol, the pyridine oxide type compound includes, for example, sodium 2-pyridinethiol-1-oxide, the inorganic salt type compound includes, for example, anhydrous sodium acetate, and the isothiazoline type compound includes, for example, 1,2-benzisothiazolin-3-one, 2-n-octyl-4-isothiazolin-3-one, 5-chloro-2-methyl-4-isothiazolin-3-one, 5-chloro-2-methyl-4-isothiazolin-3-one magnesium chloride, 5-chloro-2-methyl-4-isothiazolin-3-one calcium chloride, 2-methyl-4-isothiazolin-3-one calcium chloride and the like. The other antiseptic and fungicides include sodium sorbate, sodium benzoate and the like.

As a pH modifier, any substance can be used as long as it can control the pH of an ink in the range of 8.0 to 11.0, without impairing an ink to be formulated. Examples of the pH modifier include an alkanolamine such as diethanolamine and triethanolamine; a hydroxide of an alkali metal such as lithium hydroxide, sodium hydroxide and potassium hydroxide; an ammonium hydroxide or ammonia water; a carbonate salt of an alkali metal such as lithium carbonate, sodium carbonate, and potassium carbonate, or the like. More preferable is ammonia water.

The chelating agent includes, for example, sodium ethylenediamine tetraacetate, sodium nitrilo triacetate, sodium hydroxyethylethylenediamine triacetate, sodium diethylenetriamine pentaacetate, sodium uramil diacetate and the like.

The antirust agent includes, for example, an acidic sulfite salt, sodium thiosulfate, ammonium thioglycolate, diisopropyl ammonium nitrite, pentaerythritol tetranitrate, dicyclohexyl ammonium nitrite and the like.

The water-soluble ultraviolet absorbent includes, for example, sulfonated benzophenone, sulfonated benzotriazole or the like.

The water-soluble polymer compound includes, for example, polyvinyl alcohol, a cellulose derivative, polyamine, polyimine and the like.

The dye-dissolving agent includes, for example, urea, ε-caprolactam, ethylene carbonate and the like.

The surfactant includes, for example, anionic surfactant, amphoteric surfactant, cationic surfactant, nonionic surfactant and the like. The anionic surfactant includes an alkylsulfocarboxylate, an α-olefin sulfonate, a polyoxyethylenealkylether acetate, N-acylamino acid and a salt thereof, an N-acylmethyltaurine salt, a rosin acid soap, caster oil sulfate, lauryl alcohol sulfate, alkylphenol-type phosphoric ester, alkyl-type phosphoric ester, alkylallyl sulfonate, diethylsulfosuccinate, diethylhexyl sulfosuccinate, dioctyl sulfosuccinate and the like. The cationic surfactant includes a 2-vinylpyridine derivative, a poly 4-vinylpyridine derivative and the like. The amphoteric surfactant includes lauryldimethylaminoacetic acid betaine, 2-alkyl-N-carboxymethyl-N-hydroxyethylimidazolinium betaine, coconut oil fatty acid amide propyldimethylaminoacetic acid betaine, polyoctylpolyaminoethylglycine, and others such as imidazoline derivatives, and the like. The nonionic surfactant includes ethers such as polyoxyethylene nonylphenyl ether, polyoxyethylene octylphenyl ether, polyoxyethylene dodecylphenyl ether, polyoxyethylene octylphenyl ether, polyoxyethylene oleyl ether, polyoxyethylene lauryl ether and polyoxyethylene alkyl ether; esters such as polyoxyethylene oleic acid, polyoxyethylene oleate, polyoxyethylene distearate, sorbitan laurate, sorbitan monostearate, sorbitan monooleate, sorbitan sesquioleate, polyoxyethylene monooleate, polyoxyethylene stearate; acetylene glycols such as 2,4,7,9-tetramethyl-5-decyn-4,7-diol, 3,6-dimethyl-4-octyn-3,6-diol, 3,5-dimethyl-1-hexyn-3-ol (for example, Surfynol 104, 82, and 465, OLFINE STG and the like manufactured by Nissin Chemical Industry Co., Ltd.) and the like. These ink preparation agents are used alone or in mixture thereof.

An ink composition of the present invention can be produced by dissolving a compound represented by Formula (1) (hereinafter referred to as said coloring matter, too, for simplicity) in water or the above aqueous solvent (water containing water-soluble organic solvent), if needed, together with the above ink preparation agents and the like.

In the above production method, the sequence of dissolving each component is not especially limited. Said coloring matter may be dissolved in water or the above aqueous solvent (water containing water-soluble organic solvent) in advance and ink preparation agents may be added thereto and dissolved, otherwise after said coloring matter is dissolved in water, an aqueous solvent and ink preparation agents may be added thereto and dissolved. Also a different sequence from these may be made. Further, an aqueous solvent and ink preparation agents can be added to a solution which is a reaction solution containing said coloring matter or a dissolving solution containing said coloring matter subjected to desalting treatment with a reverse osmosis membrane, to produce an ink composition. For preparation of an ink composition, water to be used is preferably water with less impurity such as ion-exchanged water or distilled water. In addition, if required, foreign substances may be eliminated by a microfiltration method using a membrane filter and the like, and the microfiltration method is preferably performed especially when an ink composition of the present invention is used as an ink for an inkjet printer. A pore diameter of a filter to be used for the microfiltration method is typically 1 micron to 0.1 micron, preferably 0.8 micron to 0.2 micron.

A magenta ink composition containing a water-soluble anthrapyridone compound of the present invention is suitable for printing, copying, marking, writing, drawing, stamping or recording, especially inkjet recording. In this case, high quality magenta-printed articles having good fastness against water, sunlight, ozone and rubbing can be obtained. In addition, the compound of the present invention can be used to tone other colors, especially black.

A colored article of the present invention is one colored with a compound represented by Formula (1) of the present invention as mentioned above. Materials to be colored include, not particularly limited, for example, paper, textile, cloth (cellulose, nylon, wool and the like), leather, substrates for a color filter, and the like, but not limited thereto. A coloring method includes, for example, printing methods for dip dyeing, textile printing, screen printing and the like, a method by an inkjet printer, and the like, preferably a method by an inkjet printer.

A record-receiving material (media) to be used for an inkjet recording method of the present invention includes, for example, a sheet for information transmission such as paper, film and the like, textile, leather and the like. The sheet for information transmission includes preferably surface-treated one, specifically one provided with an ink receiving layer on these substrates. An ink receiving layer can be provided, for example, by impregnating or coating cationic polymer on the above substrates, or by coating porous white inorganic substance such as porous silica, aluminasol or special ceramics and the like which can adsorb coloring matter in the ink on the surface of the above substrate together with a hydrophilic polymer such as polyvinylalcohol, polyvinylpyrrolidone and the like. Such articles provided with an ink receiving layer are usually called inkjet paper (film) or glossy paper (film), and available from the market as, for example, Pictorico (trade name; manufactured by Asahi Glass Co., Ltd.), Professional Photopaper, Super Photopaper, and Matte Photopaper (trade names; all manufactured by Canon Inc.), Photograph Paper (glossy), Photo Matte Paper and Super Fine Glossy Film (trade names; all manufactured by SEIKO-EPSON CORPORATION), Premium Plus Photo Paper, Premium Glossy Film and Photo Paper (trade names; all manufactured by Hewllet Packard, Japan Ltd.), PhotoLikeQP (trade name; manufactured by Konica Minolta, Japan), and the like. In addition, naturally plain paper can be used.

Among them, it is known that discoloration or fading of an image recorded on a record-receiving material of which the surface is coated with porous white inorganic substance is proceeded especially further by ozone gas, but a water-based magenta ink composition of the present invention is so superior in gas fastness that it has an effect especially in recording on such a record-receiving material.

The porous white inorganic substance to be used for such a purpose is calcium carbonate, kaolin, talc, clay, diatom earth, synthetic amorphous silica, aluminum silicate, magnesium silicate, calcium silicate, aluminium hydroxide, alumina, lithopone, zeolite, barium sulfate, calcium sulfate, titanium dioxide, zinc sulfide, zinc carbonate or the like.

For recording on a record-receiving material by means of the inkjet recording method of the present invention, for example, a container containing the above ink composition is set on a predefined position in an inkjet printer and recording may be performed on a record-receiving material in a conventional manner. In the inkjet recording method of the present invention, in addition to a yellow ink composition and a cyan ink composition as known and used, a green ink composition, an orange ink composition, a blue (or violet) ink composition, a magenta ink composition of the present invention, if required, a black ink composition and the like can be used in combination. Each color ink composition is injected into each container, and the containers, as well as a container containing a water-based magenta ink composition for inkjet recording of the present invention, are set (loaded) in predefined positions in an inkjet printer to be used. The inkjet printer to be used includes, for example, a printer of piezo method utilizing mechanical vibration, a printer of Bubble Jet (registered trademark) method utilizing bubbles generated by heating, and the like.

A water-based magenta ink composition of the present invention is a vivid magenta color, especially has a highly vivid hue on inkjet glossy paper, and provides high fastness of a recorded image. It also gives high safety to human being.

An ink composition according to the present invention doesn't cause sedimentation and separation during storage. When an ink composition according to the present invention is used in inkjet recording, the injector (ink head) is not clogged. An ink according to the present invention doesn't cause change in physical properties even when used under constant recirculation for a relatively long period of time by a continuous inkjet printer or used intermittently by an on-demand inkjet printer.

Hereinafter, the present invention will be more specifically explained by Examples. In this connection, "part" and "%" hereinafter in the description are based on weight unless otherwise specified.

Example 1

(1) Into 360 parts of xylene, 94.8 parts of a compound represented by Formula (11) (R=$CH_3$), 3.0 parts of sodium carbonate and 144.0 parts of ethyl benzoylacetate were charged sequentially while stirring, followed by temperature rise. The reaction was conducted at a temperature of 140 to 150° C. for 8 hours, and meanwhile ethanol and water produced from the reaction were distilled out of the system by azeotropy with xylene to complete the reaction. Subsequently, after the resultant was cooled and 240 parts of methanol was added thereto at 30° C. followed by stirring for 30 minutes, the precipitate was separated by filtration and the resulting precipitate was washed with 360 parts of methanol and dried to obtain 124.8 parts of a compound represented by Formula (12) (R=$CH_3$) as a pale yellow needle crystal.

(2) Secondly, into 300.0 parts of N,N-dimethylformamide, 88.8 parts of a compound (R=$CH_3$) of Formula (12), 75.0 parts of meta amino acetanilide, 24.0 parts of copper acetate monohydrate and 12.8 parts of sodium carbonate were charged sequentially while stirring, followed by temperature rise. The reaction was conducted at 120 to 130° C. for 3 hours. After 120 parts of methanol was added thereto under cooling to approximately 50° C. and stirred for 30 minutes, the precipitate was separated by filtration and the resulting precipitate was washed with 500 parts of methanol and then washed with hot water of 80° C. followed by drying to obtain 79.2 parts of a compound represented by Formula (13) (R=$CH_3$) as a blue-tinged red crystal.

(3) Next, to 130 parts of 98.0% sulfuric acid, 170.0 parts of 28.0% fuming sulfuric acid was added under stirring while water cooling to prepare 300 parts of 12% fuming sulfuric acid. Under water cooling, 51.3 parts of a compound represented by Formula (13) (R=$CH_3$) was added to the resulting fuming sulfuric acid at no higher than 50° C., followed by temperature rise. The reaction (sulfonation) was conducted at 85 to 90° C. for 4 hours. Subsequently, the sulfonation reaction solution obtained above was added in 600 parts of ice water. In the meantime, the solution temperature was maintained at no higher than 40° C. while adding ice. Water was added to the obtained solution to bring the liquid volume to 1000 parts, followed by filtration to eliminate insoluble content. Subsequently, hot water was added to the mother liquid to bring the volume to 1500 parts, 300 parts of sodium chloride was added thereto and stirred for 2 hours while maintaining the temperature at 60 to 65° C., and the precipitated crystal was separated by filtration. The obtained crystals were washed with 300 parts of 20% sodium chloride aqueous solution and squeezed to obtain 100.3 parts of a wet cake (degree of purity: 45.9% by a diazo analysis method; the same hereinafter) containing 59.2 parts of a compound represented by Formula (7) (R=$CH_3$) as a red crystal.

(4) In 60 parts of water, 67.7 parts of a wet cake (degree of purity; 45.9%) of the compound represented by Formula (7) obtained in the above (3) was added, then 24 parts of 25% caustic soda was added followed by stirring, and dissolved while adjusting the pH at 3 to 4 by further additional of 25% caustic soda. Meanwhile, after 0.4 parts of Lipall OH (trade name; anionic surfactant manufactured by Lion Corporation) was added to 60 parts of ice water and dissolved, 8.9 parts of cyanuric chloride was added followed by stirring for 30 minutes. The resulting suspension was added in the solution containing a compound of the above Formula (7) and subjected to a first condensation reaction at 25 to 30° C. for 3 hours while 10% caustic soda aqueous solution was added dropwise thereto to maintain the pH at 2.7 to 3.0 and a reaction solution containing a compound represented by Formula (8) (R=$CH_3$) was obtained.

(5) In the reaction solution containing the compound represented by Formula (8) (R=$CH_3$) obtained in the above (4), ice was added to adjust the temperature at 5° C. Subsequently, 25% caustic soda aqueous solution was added dropwise to adjust the pH at 9. Separately, to 40 parts of water, 7.7 parts of 5-hydroxyisophthalic acid and 25% caustic soda aqueous solution were added to obtain an aqueous solution with the pH adjusted at 9. In the above reaction solution of 5° C., said aqueous solution was added dropwise over 30 minutes. In the meanwhile, ice and 25% caustic soda aqueous solution was added thereto to maintain the temperature at 5 to 10° C. and the pH at 9.0±0.3. The solution was then heated to a temperature of 27 to 30° C. while maintaining the pH at 9±0.3 by dropwise addition of 25% caustic soda aqueous solution. The reaction was conducted for 1 hour at the temperature and the reaction was completed to obtain a reaction solution containing a compound represented by Formula (9) (R=$CH_3$, Y=3,5-dicarboxyphenoxy group).

(6) In the reaction solution containing the compound represented by Formula (9) (R=$CH_3$, Y=3,5-dicarboxyphenoxy group) obtained in the above (5), 1.2 parts of ethylenediamine was added, the pH was maintained at 8.7 to 9.3 by dropwise addition of 25% caustic soda aqueous solution, and the reaction was conducted for 1 hour at a temperature of 87 to 93° C. After the reaction, water was added to adjust the liquid volume to approximately 350 parts followed by filtration to eliminate insoluble substance.

Water was added to the resulting reaction solution to adjust the liquid volume to 400 parts. Concentrated hydrochloric acid was added to adjust the pH at 3 while maintaining the temperature at 65±2° C. Subsequently, 40 parts of sodium chloride was added over 15 minutes followed by stirring for 1 hour, and the precipitated crystal was separated by filtration and washed with 150 parts of 20% sodium chloride aqueous solution to obtain a compound represented by the following Formula (15) (Compound No. 1 in Table 1) as a red wet cake.

(7) The wet cake obtained in the above (6) was added in 700 parts of methanol and maintained to 60 to 65° C. for 1 hour while heating and stirring. The crystal was then separated by filtration, washed with methanol and dried to obtain 35.1 parts of a compound represented by the following Formula (15) as a red crystal. The maximum absorption wavelength: 510 and 529 nm (in an aqueous solution)

[KA 18]

(15)

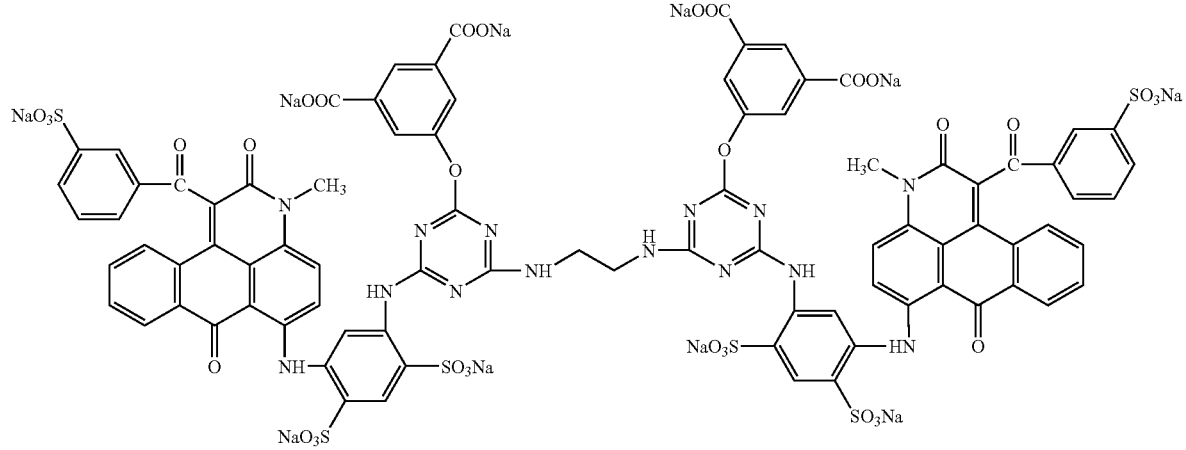

Example 2

(1) In a reaction solution containing a compound represented by Formula (9) (R=CH₃, Y=3,5-dicarboxyphenoxy group) obtained in the same manner as in (1) to (5) of Example 1, 1.9 parts of 1,2-ethandithiol was added and further water was added thereto to bring the liquid volume to 400 parts, followed by temperature rise. The reaction was conducted for 1 hour at a temperature of 85 to 90° C. with the pH maintained at 7.8 to 8.2 by dropwise addition of 25% caustic soda aqueous solution. After the reaction, water was added to adjust the liquid volume to approximately 430 parts, followed by filtration to eliminate insoluble substance. Water was added to the obtained reaction solution to adjust the liquid volume to 450 parts. Concentrated hydrochloric acid was added thereto to adjust the pH at 3 while maintaining the temperature at 55 to 60° C. Subsequently, 40 parts of sodium chloride was added over 15 minutes followed by stirring for 1 hour, and the precipitated crystal was separated by filtration and washed with 250 parts of 15% sodium chloride aqueous solution to obtain a compound represented by the following Formula (16) (Compound No. 10 in Table 1) as a red wet cake.

(2) The wet cake obtained in the above (1) was added in 500 parts of methanol and maintained to 60 to 65° C. for 1 hour while heating and stirring. The precipitated crystal was then separated by filtration, washed with methanol and dried to obtain 26.4 parts of a compound represented by the following Formula (16) as a red crystal.

The maximum absorption wavelength: 507 and 533 nm (in an aqueous solution)

[KA 19]

(16)

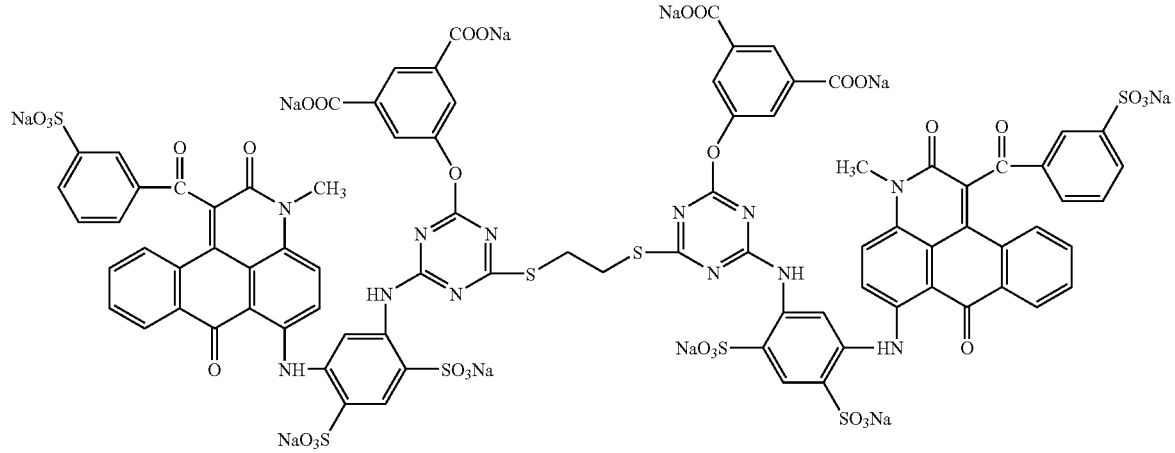

Example 3

(1) In a reaction solution containing a compound represented by Formula (9) (R=CH₃, Y=3,5-dicarboxyphenoxy group) obtained in the same manner as in (1) to (5) of Example 1, 4.2 parts of 4,4'-diaminodicyclohexyl methane was added and further water was added to bring the liquid volume to 400 parts, followed by temperature rise. The reaction was conducted for 1 hour at a temperature of 85 to 90° C. with the pH maintained at 8.8 to 9.2 by dropwise addition of 25% caustic soda aqueous solution. After the reaction, water was added to adjust the liquid volume to approximately 450 parts, followed by filtration to eliminate insoluble substance.

Water was added to the resulting reaction solution to adjust the liquid volume to 500 parts. Concentrated hydrochloric acid was added thereto to adjust the pH at 2 while maintaining the temperature at 60 to 65° C. Subsequently, 50 parts of sodium chloride was added over 15 minutes followed by stirring for 1 hour, and the precipitated crystal was separated by filtration and washed with 300 parts of 15% sodium chloride aqueous solution to obtain a compound represented by the following Formula (17) (Compound No. 2 in Table 1) as a red wet cake.

(2) The wet cake obtained in the above (1) was added in 500 parts of methanol and maintained to 60 to 65° C. for 1 hour while heating and stirring. The precipitated crystal was then separated by filtration, washed with methanol and dried to obtain 18.9 parts of a compound represented by the following Formula (17) as a red crystal.

The maximum absorption wavelength (λmax): 536 nm (in an aqueous solution)

[KA 20]

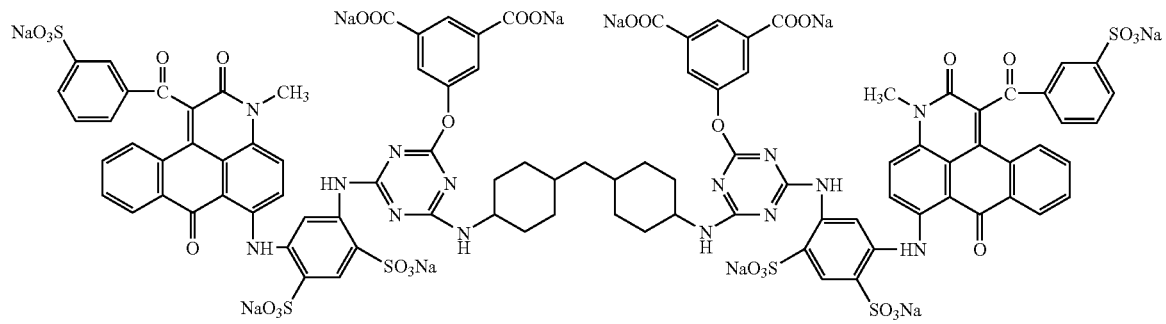

(17)

Example 4

(1) In a reaction solution containing a compound represented by Formula (9) (R=CH₃, Y=3,5-dicarboxyphenoxy group) obtained in the same manner as in (1) to (5) of Example 1, 1.3 parts of 80% aqueous solution of hydrazine monohydrate was added and further water was added to bring the liquid volume to 400 parts, followed by temperature rise. The reaction was conducted for 1 hour at a temperature of 85 to 90° C. with the pH maintained at 8.8 to 9.2 by dropwise addition of 25% caustic soda aqueous solution. After the reaction, water was added to adjust the liquid volume to approximately 450 parts, followed by filtration to eliminate insoluble substance.

Water was added to the resulting reaction solution to bring the liquid volume to 500 parts. Concentrated hydrochloric acid was added thereto to adjust the pH at 3 while maintaining the temperature at 55 to 60° C. Subsequently, 50 parts of sodium chloride was added over 15 minutes followed by stirring for 1 hour, and the precipitated crystal was separated by filtration and washed with 250 parts of 15% sodium chloride aqueous solution to obtain a compound represented by the following Formula (18) (Compound No. 3 in Table 1) as a red wet cake.

(2) The wet cake obtained in the above (1) was added in 500 parts of methanol and maintained to 60 to 65° C. for 1 hour while stirring and heating. The precipitated crystal was then separated by filtration, washed with methanol and dried to obtain 16.0 parts of a compound represented by the following Formula (18) as a red crystal.

The maximum absorption wavelength (λmax): 533 nm (in an aqueous solution)

[KA 21]

(18)

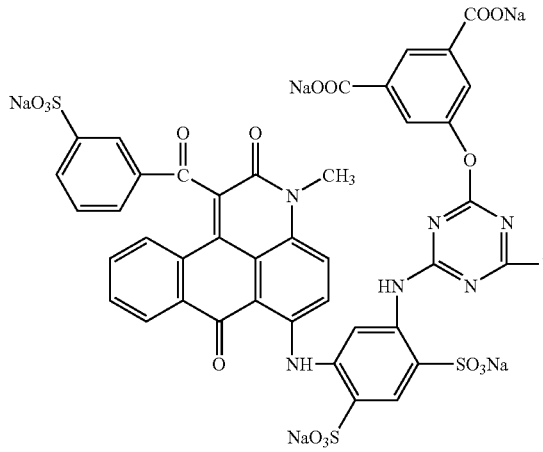

Example 5

(1) In a reaction solution containing a compound represented by Formula (8) (R=CH$_3$) obtained in the same manner as in (1) to (4) of Example 1, ice was added to adjust the temperature at 7° C. Subsequently, 25% caustic soda aqueous solution was added dropwise to adjust the pH at 9. Separately, 6.8 parts of 4-hydroxybenzoic acid and 25% caustic soda aqueous solution were added to 40 parts of water to obtain an aqueous solution with the pH adjusted at 9. In the above reaction solution having a temperature of 7° C., said aqueous solution was added dropwise over 30 minutes. In the meanwhile, ice and 25% caustic soda aqueous solution was added thereto to maintain the temperature at 5 to 10° C. and the pH at 9.0±0.3. The solution was then heated to a temperature of 40 to 50° C. while maintaining the pH at 8.7 to 9.3 by dropwise addition of 25% caustic soda aqueous solution. The reaction was conducted for 1 hour at the temperature and completed to obtain a reaction solution containing a compound represented by Formula (9) (R=CH$_3$, Y=4-carboxyphenoxy group).

(2) In the reaction solution containing a compound represented by Formula (9) (R=CH$_3$, Y=4-carboxyphenoxy group) obtained in the above (1), 1.2 parts of ethylenediamine was added, the pH was maintained at 8.7 to 9.3 by dropwise addition of 25% caustic soda aqueous solution, and the reaction was conducted for 1 hour at a temperature of 87 to 93° C. After the reaction, water was added to adjust the liquid volume to approximately 350 parts followed by filtration to eliminate insoluble substance. Water was added to the resulting reaction solution to adjust the liquid volume to 600 parts. Concentrated hydrochloric acid was added to adjust the pH at 1 while maintaining the temperature at 65±2° C. Subsequently, 108 parts of sodium chloride was added over 15 minutes followed by stirring for 1 hour and the precipitated crystal was separated by filtration and washed with 400 parts of 20% sodium chloride aqueous solution to obtain a compound represented the following Formula (19) (Compound No. 4 in Table 1) as a red wet cake.

(3) The wet cake obtained in the above (2) was added to 600 parts of methanol and maintained to 60 to 65° C. for 1 hour while heating and stirring. The precipitated crystal was then separated by filtration, washed with methanol and dried to obtain 16.3 parts of a compound represented by the following Formula (19) as a red crystal.

The maximum absorption wavelength: 511 nm and 530 nm (in an aqueous solution)

[KA 22]

(19)

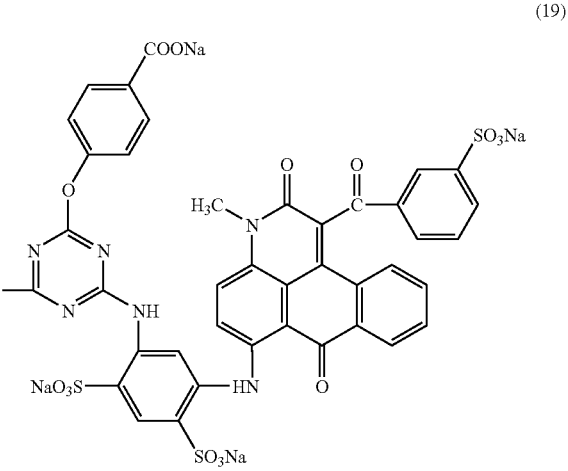

Examples 6 to 10

(A) Preparation of Ink

An ink composition shown in the following Table 2 was prepared using a compound (Compound Example No. 1) obtained in the above Example 1, followed by filtration with a 0.45 μm membrane filter to obtain a water-based magenta ink composition of the present invention. In addition, ion-exchanged water and ammonia water were added to the ink composition in order to adjust the pH at 8 to 10 and bring the total amount to 100 parts. Example 6 is for the ink composition obtained using a compound obtained in Example 1. Similarly Examples 7 to 10 are respectively for the ink compositions obtained by using the compounds obtained in Examples 2 to 5. Further, as a comparative object (Comparative Example), an ink composition for comparison was produced from the composition shown in Table 2 by using a compound of Example 3 in Patent Literature 8 (compound No. 20). Inkjet recording was conducted using said ink composition and evaluation of a recorded image was performed (only on fastness for the comparative example). The results are shown in Table 3 and Table 4.

TABLE 2

| (Composition of ink composition) | |
|---|---|
| Compound of Example 1 (Compound Example No. 1) | 6.0 parts |
| Glycerin | 5.0 parts |
| Urea | 5.0 parts |
| N-methyl-2-pyrrolidone | 4.0 parts |
| Isopropyl alcohol | 3.0 parts |
| Butylcarbitol | 2.0 parts |
| Surfynol 104PG50 (manufactured by Nissin Chemical Industry Co., Ltd.) | 0.1 part |
| Ion-exchanged water + ammonia water | 74.9 parts |
| Total | 100.0 parts |

(B) Inkjet Printing

Using an inkjet printer (trade name: Pixus 860i manufactured by Canon Inc.), inkjet recording was conducted on glossy paper having an ink-receiving layer containing porous white inorganic substance (Professional Photopaper PR-101 manufactured by Canon Inc. and Photo Paper (Glossy) manufactured by SEIKO-EPSON CORPORATION). In inkjet recording, an image pattern was made so as to obtain gradations of several stages in printing density, and a print was made.

(C) Evaluation of Recorded Images (1) Evaluation of Hue for Recorded Images on Glossy Paper Hue and vividness in recorded images: Images on recorded paper were measured using a colorimetric system (GRETAG SPM50 manufactured by Gretag Macbeth AG.), evaluation was performed using values of L*, a* and b* calculated by said system and values of vividness (C*) calculated from chromaticity (a* and b*) using the following formula.

$$C^* = ((a^*)^2 + (b^*)^2)^{1/2}$$

The evaluation was performed on hue and vividness by comparing with a sample of standard magenta in Japan Color manufactured by JNC (Industry Association: Japan Printing Machinery Association).

The values of hue and vividness of recorded images obtained using the ink compositions of Examples 6 to 10 are shown in Table 3 together with values of a sample of standard magenta in Japan Color. In this connection, the paper of standard magenta in Japan Color is Japan Color Standard Paper.

TABLE 3

| | hue | | | vividness |
|---|---|---|---|---|
| | L* | a* | b* | C* |
| JNC standard magenta | 46.3 | 74.4 | −4.8 | 74.6 |
| Glossy paper manufactured by CANON Inc. | | | | |
| Example 6 (No. 1) | 52.4 | 76.4 | −26.1 | 80.8 |
| Example 7 (No. 10) | 51.8 | 76.9 | −25.8 | 81.1 |
| Example 8 (No. 2) | 53.4 | 77.9 | −26.9 | 82.4 |
| Example 9 (No. 3) | 50.3 | 74.8 | −30.7 | 80.8 |
| Example 10 (No. 4) | 53.5 | 76.1 | −26.2 | 80.3 |
| Glossy paper manufactured by SEIKO-EPSON CORPORATION. | | | | |
| Example 6 (No. 1) | 54.5 | 77.4 | −25.2 | 81.4 |
| Example 7 (No. 10) | 57.0 | 78.6 | −27.3 | 83.2 |
| Example 8 (No. 2) | 53.4 | 77.8 | −29.5 | 83.2 |
| Example 9 (No. 3) | 50.2 | 75.8 | −33.6 | 83.0 |
| Example 10 (No. 4) | 54.3 | 76.7 | −27.1 | 81.3 |

Judging from Table 3, it is found that the hue of any glossy paper approximates that of JNC standard magenta in the case of using a magenta ink composition of the present invention (Example 6 to 10) and the magenta ink composition of the present invention is suitable for a magenta ink composition for inkjet. In addition, C* values of images using a magenta ink composition of the present invention are higher than the value of JNS standard magenta. Judging from these results, it is found that an anthrapyridone compound of the present invention provides hue with excellent vividness as coloring matter for magenta.

(2) Xenon Light Fastness Test of a Recorded Image

Using a xenon weatherometer Ci4000 (trade name: manufactured by ATLAS Electric Devices Co.), pieces of printed testing paper of glossy paper manufactured by Canon, Inc. and glossy paper manufactured by SEIKO-EPSON CORPORATION, on which an air layer was provided and a glass plate having a thickness of 2 mm was set up, were irradiated for 50 hours at an illuminance of 0.36 W/m² under conditions of a humidity of 60% RH and a temperature of 24° C. From color differences (ΔE) before and after the test, the evaluation was performed on 3 levels based on the following criteria.

ΔE≦10 . . . ○

10<ΔE≦20 . . . Δ

ΔE>20 . . . x

Each value of L*, a* and b* before and after the test was measured using the above calorimetric system (GRETAG SPM50: manufactured by GRETAG Macbeth AG) and color difference (ΔE) was calculated from the difference before and after the test of each value of L*, a* and b* using the following formula.

$$\Delta E = ((\text{difference of } L^*)^2 + (\text{difference of } a^*)^2 + (\text{difference of } b^*)^2)^{1/2}$$

The results are shown in Table 4.

(3) Ozone Gas Fastness Test of a Recorded Image

Using an ozone weatherometer (trade name: manufactured by Suga Test Instruments Co., Ltd.), pieces of printed testing paper of glossy paper manufactured by Canon, Inc. and manufactured by SEIKO-EPSON CORPORATION were left for 6 hours under the circumstances of an ozone concentration of 40 ppm, a humidity of 60% RH and a temperature of 24° C. From color differences (ΔE) before and after the test obtained in the same manner as in the above (2), the evaluation was performed on 3 levels based on the following criteria.

ΔE ≦ 20 . . . ○

20 < ΔE ≦ 40 . . . Δ

ΔE > 40 . . . x

The results are shown in Table 4.

(4) Moisture Fastness Test of Recorded Images

Using a thermo-hygrostat (manufactured by OHKEN, Co., LTD), pieces of printed testing paper of glossy paper manufactured by Canon, Inc. and manufactured by SEIKO-EPSON CORPORATION were left for 168 hours under the conditions of a temperature of 50° C. and a humidity of 90% RH. Bleeding before and after the test was determined by visual observation and evaluated on 3 levels based on the following criteria.

○: Bleeding is not observed.

Δ: Bleeding is observed on small degree.

x: Bleeding is observed on large degree.

The results are shown in Table 4.

TABLE 4

|  | light fastness | ozone fastness | moisture fastness |
| --- | --- | --- | --- |
| Glossy paper manufactured by CANON INC. | | | |
| Example 6 (No. 1) | ○ | ○ | ○ |
| Example 7 (No. 10) | ○ | ○ | ○ |
| Example 8 (No. 2) | ○ | ○ | ○ |
| Example 9 (No. 3) | ○ | ○ | ○ |
| Example 10 (No. 4) | ○ | ○ | ○ |
| Comparative Example 1 | Δ | Δ | ○ |
| Glossy paper manufactured by SEIKO-EPSON CORPORATION. | | | |
| Example 6 (No. 1) | ○ | ○ | ○ |
| Example 7 (No. 10) | ○ | ○ | ○ |
| Example 8 (No. 2) | ○ | ○ | ○ |
| Example 9 (No. 3) | ○ | ○ | Δ-○ |
| Example 10 (No. 4) | ○ | ○ | ○ |
| Comparative Example 1 | Δ | ○ | Δ |

Judging from Table 4, it is found that an anthrapyridone compound of the present invention is coloring matter providing an image which is extremely excellent in light fastness, ozone fastness and moisture fastness.

INDUSTRIAL APPLICABILITY

An anthrapyridone compound represented by Formula (1) of the present invention is suitable magenta coloring matter for inkjet recording because said compound has high solubility in water and suitable hue and vividness for inkjet recording, a magenta ink composition containing said compound is excellent in storage stability, and also a recorded article by using said ink is excellent in light fastness, moisture fastness and gas fastness.

The invention claimed is:

1. An anthrapyridone compound represented by the following Formula (1)

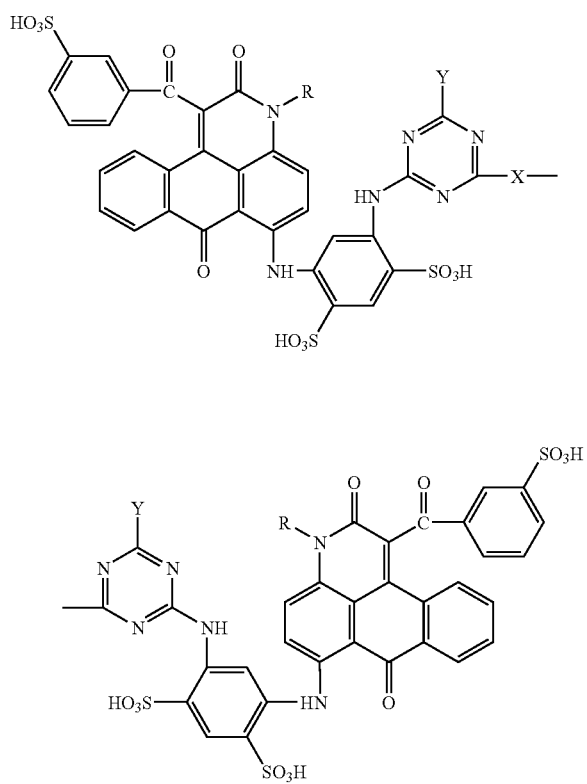

wherein R represents a hydrogen atom, an alkyl group, a hydroxy lower alkyl group, a cyclohexyl group, a mono- or dialkylaminoalkyl group or a cyano lower alkyl group, X represents NH—NH, S—CH$_2$CH$_2$—S, NH—CH$_2$CH$_2$—NH or NH-cyclohexyl-CH$_2$-cyclohexyl-NH, Y represents 4-carboxyphenoxy group or a 3,5-dicarboxyphenoxy group, in free acid form.

2. The anthrapyridone compound according to claim 1, which is represented by the following Formula (3)
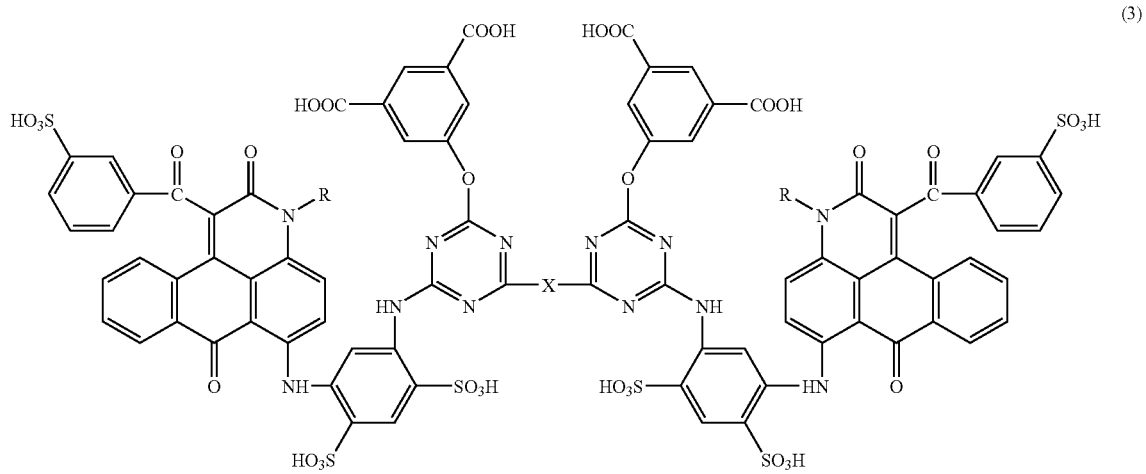
(3)
wherein R and X have the same meanings as in Formula (1) in free acid form.
3. The anthrapyridone compound according to claim 1, which is represented by Formula (4)
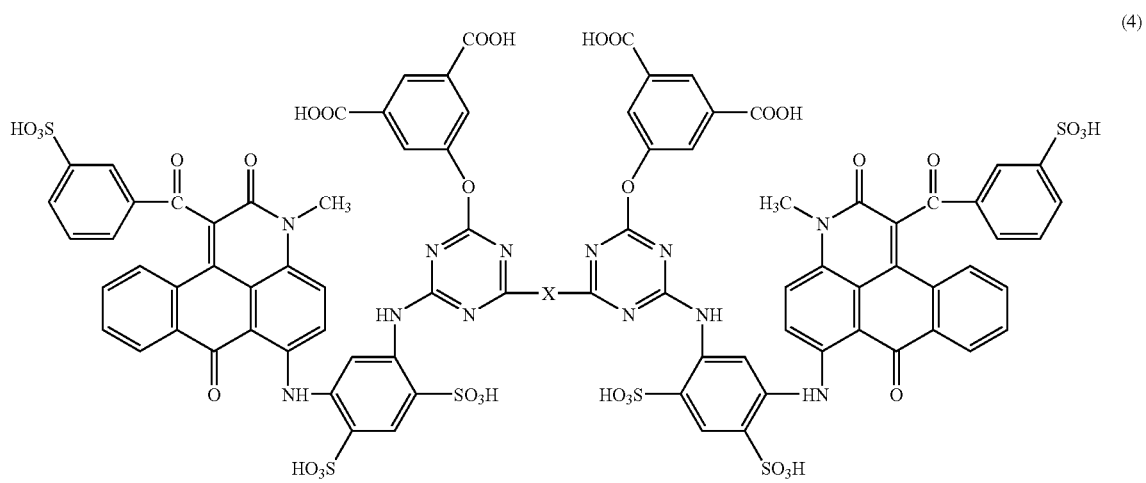
(4)
wherein X has the same meaning as in Formula (1) in free acid form.

4. An anthrapyridone compound represented by the following Formula (5)

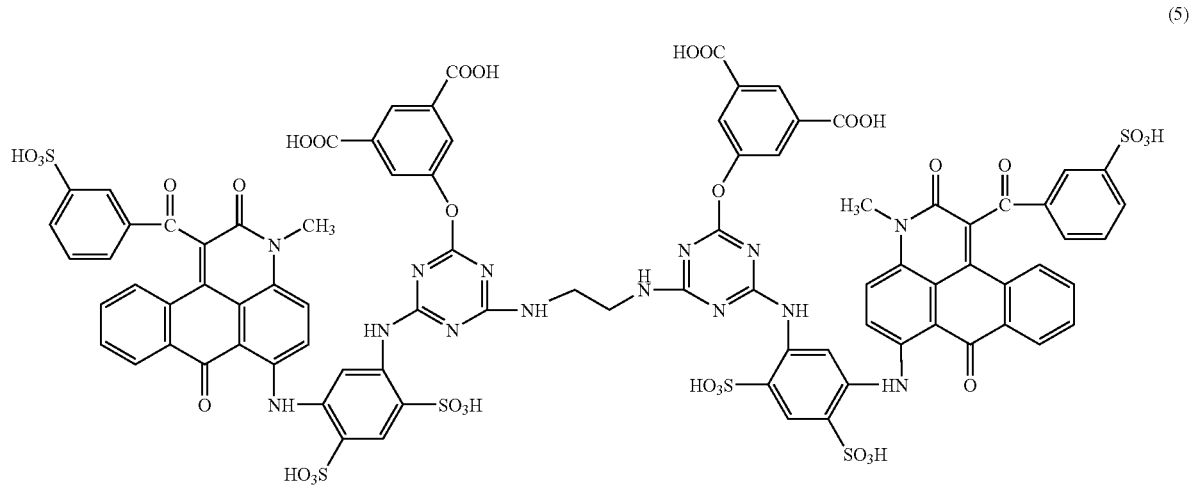

(5)

in free acid form.

5. An anthrapyridone compound represented by the following Formula (6)

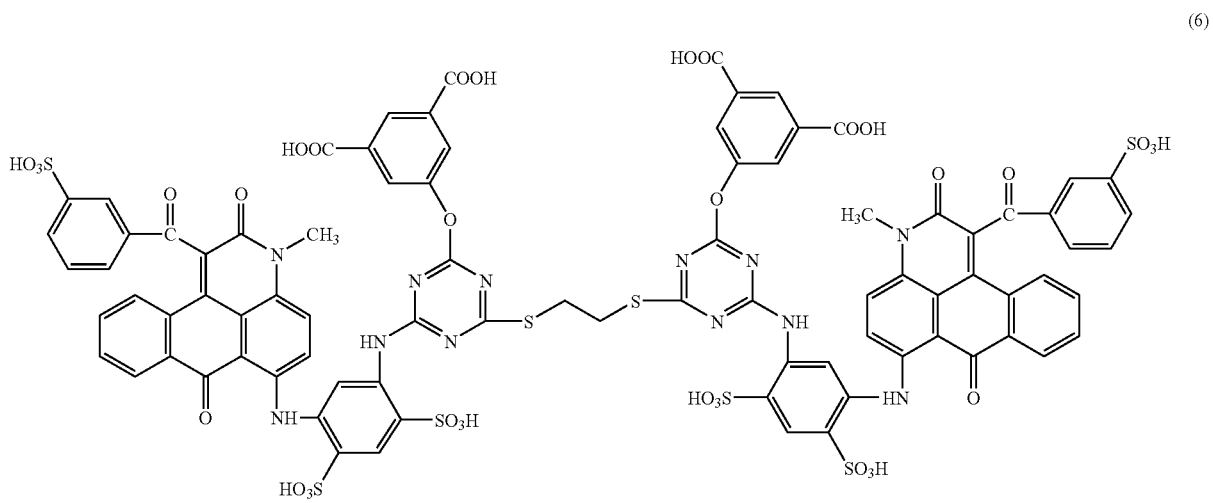

(6)

in free acid form.

6. A magenta ink composition comprising the anthrapyridone compound according to claim 1.

7. The magenta ink composition according to claim 6, which comprises water and a water-soluble organic solvent.

8. The magenta ink composition according to claim 7, which is for inkjet.

9. The magenta ink composition according to claim 6, wherein the content of inorganic substance in the anthrapyridone compound is not more than 1 weight %.

10. The magenta ink composition according to claim 6, wherein the content of the anthrapyridone compound is 0.1 to 20 weight %.

11. A magenta ink composition comprising the anthrapyridone compound according to any one of claim 4 or 5.

12. An inkjet recording method comprising discharging an ink droplet on a record-receiving material in response to a recording signal, wherein said ink droplet comprises the magenta ink composition according to claim 6.

13. The inkjet recording method according to claim 12, wherein the record-receiving material is a sheet for information transmission.

14. The inkjet recording method according to the above claim 13, wherein the sheet for information transmission has an ink-receiving layer comprising porous white inorganic substance.

15. A colored article which is colored with the magenta ink composition according to claim 6.

16. The colored article according to claim 15, wherein coloring is performed by an inkjet printer.

17. An inkjet printer wherein a container comprising the magenta ink composition according to claim 6 is loaded.

* * * * *